United States Patent [19]

Jacobsen et al.

[11] Patent Number: 5,328,224

[45] Date of Patent: Jul. 12, 1994

[54] ROBOTIC GRASPING APPARATUS

[75] Inventors: Stephen C. Jacobsen; Fraser Smith, both of Salt Lake City, Utah

[73] Assignee: University of Utah Research Foundation, Salt Lake City, Utah

[21] Appl. No.: 58,690

[22] Filed: May 7, 1993

Related U.S. Application Data

[63] Continuation of Ser. No. 963,831, Oct. 20, 1992, abandoned, which is a continuation of Ser. No. 563,399, Aug. 6, 1990, Pat. No. 5,172,951.

[51] Int. Cl.$^5$ .............................................. B25J 15/10
[52] U.S. Cl. ................................... 294/104; 294/106; 901/39
[58] Field of Search ............... 294/104, 106; 901/30, 901/31, 39; 623/63, 64

[56] References Cited

U.S. PATENT DOCUMENTS

| | | | |
|---|---|---|---|
| 2,540,375 | 2/1951 | Motis | 623/64 |
| 3,173,151 | 3/1965 | Glabiszewski | 623/64 |
| 3,866,966 | 2/1975 | Skinner, II | 294/106 |
| 3,901,547 | 8/1975 | Skinner, II | 294/106 X |
| 4,225,983 | 10/1980 | Radocy et al. | 623/64 X |
| 4,332,038 | 6/1982 | Freeland | 623/64 |
| 4,921,293 | 5/1990 | Ruoff et al. | 294/106 X |
| 4,946,380 | 8/1990 | Lee | 623/64 X |
| 4,957,320 | 9/1990 | Ulrich | 294/106 |

*Primary Examiner*—Dean J. Kramer
*Attorney, Agent, or Firm*—Thorpe North & Western

[57] ABSTRACT

A robotic grasping manipulator includes a support base, a fixed elongate index finger which extends forwardly a certain distance from the base and then curves upwardly to terminate in a tip, and a two-degree of freedom elongate thumb pivotally attached at a proximal end to the base to extend generally forwardly therefrom to terminate in a distal end which may be moved vertically and laterally with respect to the fixed finger to thereby enable holding objects between the finger and thumb. Also included is a moveable elongate finger pivotally attached at a proximal end to the base to extend forwardly a certain distance and then upwardly, generally alongside the index finger, to terminate in a distal end. The distal end may be moved laterally away from and toward the index finger to thereby enable holding objects between the two fingers. With the two-degree of freedom movement of the thumb and the one-degree of freedom movement of the moveable finger, a variety of different shaped objects may be grasped and held between the two fingers and thumb.

12 Claims, 4 Drawing Sheets

ROBOTIC GRASPING APPARATUS

This application is a continuation of U.S. application Ser. No. 07/963,831, filed Oct. 20, 1992 now abandoned, which is a continuation of prior application Ser. No. 07/563,399 filed on Aug. 6, 1990 now U.S. Pat. No. 5,172,951 of STEPHEN C. JACOBSEN et al. for ROBOTIC GRASPING APPARATUS.

BACKGROUND OF THE INVENTION

This invention relates to robotic apparatus and more particularly to grasping and manipulating apparatus.

Robotic devices and implements have been used in a variety of fields where direct human involvement is either too hazardous, too inefficient, or too monotonous and tiring. Examples of such fields include manufacturing where robots are used to carry out pickup and assembly of parts, welding, nailing and riveting, etc., handling of hazardous material such as radioactive products where direct human handling could pose a health risk, and remote handling or manipulation of articles, control panels, or other structures where on-site location of humans is desirable or possible. Also, more sophisticated, efficient and dexterous robotic apparatus is being sought for use as artificial limbs. This is especially true for implements to enable grasping and holding in a manner similar to the grasping and holding ability of the human hand.

Robotic grasping implements currently available range from the simple two jaw gripping device formed similar to the jaws of a pair of pliers, to the more complicated artificial hands having three or four fingers and a thumb which may be operated to curl about objects to be grasped. In both the simple and complicated grasping implements, while larger objects can oftentimes be handled, smaller or thinner objects cannot be, especially if such objects must be picked up from a flat surface for example. Also, the number of positions or orientations in which graspable objects can be held is generally very limited with currently available grasping implements.

SUMMARY OF THE INVENTION

It is an object of the invention to provide a robotic grasping apparatus with anthropomorphic characteristics.

It is another object of the invention to provide a simple and easy to control robotic grasping apparatus.

It is a further object of the invention to provide a grasping apparatus which is capable of holding and picking up small and thin objects as well as larger objects.

It is an additional object of the invention to provide a versatile grasping apparatus for holding objects having a variety of sizes and shapes.

It is still another object of the invention to provide such an apparatus capable of holding objects in a variety of positions and orientations.

The above and other objects of the invention are realized in a specific illustrative embodiment of a robotic grasping apparatus which includes a fixed finger having a base section, a narrowed middle section extending outwardly from the base section, and a curved end section which extends outwardly and upwardly from the middle section to terminate in a tip. Also included is an elongate moveable thumb having a fixed end mounted in the base of the finger to pivot selectively about either of two axes which are generally at right angles to one another and which both extend laterally of the long axis of the thumb, and a free end selectively moveable to a position in contact with the end of the tip of the finger and to positions in contact with either side of the tip of the finger.

In accordance with one aspect of the invention, a moveable finger is also provided in which a base end thereof is pivotally mounted to the fixed finger so that a free end of the moveable finger may be pivoted toward and away from the end section of the fixed finger. With the thumb, which moves in two degrees of freedom, the moveable finger, which moves in one degree of freedom, and the fixed finger, thin objects may be held between the thumb and either the fixed finger or moveable finger, small objects may be held between the thumb and fixed finger or between the thumb, fixed finger and moveable finger, and more bulky or elongate objects be held between the two fingers and the thumb.

In accordance with another aspect of the invention, the distal surfaces of the tip of the fixed finger and the free end of the thumb are co-convex when the thumb is pivoted into contact with the fixed finger. This enables picking up of small objects from a flat surface area, for example.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Referring to FIGS. 1-4, there are shown various views of one specific illustrative embodiment of a robotic grasping apparatus illustrating the principles of the present invention. This apparatus includes a housing or base 4 from which two fingers and a thumb, to be described, project and in which are contained control mechanisms for controlling the movement of one of the fingers and the thumb. The base 4 might illustratively be joined to a jointed robotic arm or other similar robotic structure by support bars 6 to enable positioning the grasping apparatus in different orientations. Such robotic arms are known in the art.

Figure 1:
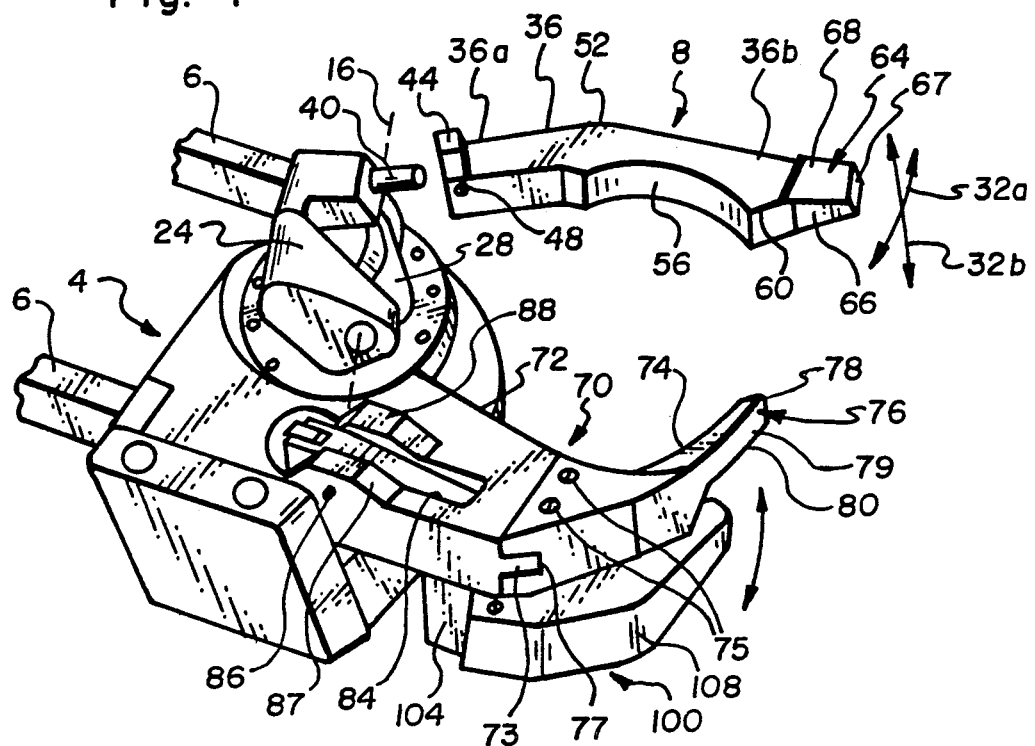
FIG. 1 is a perspective, partially exploded view of a robotic grasping apparatus made in accordance with the principles of the present invention.
Figure 2:
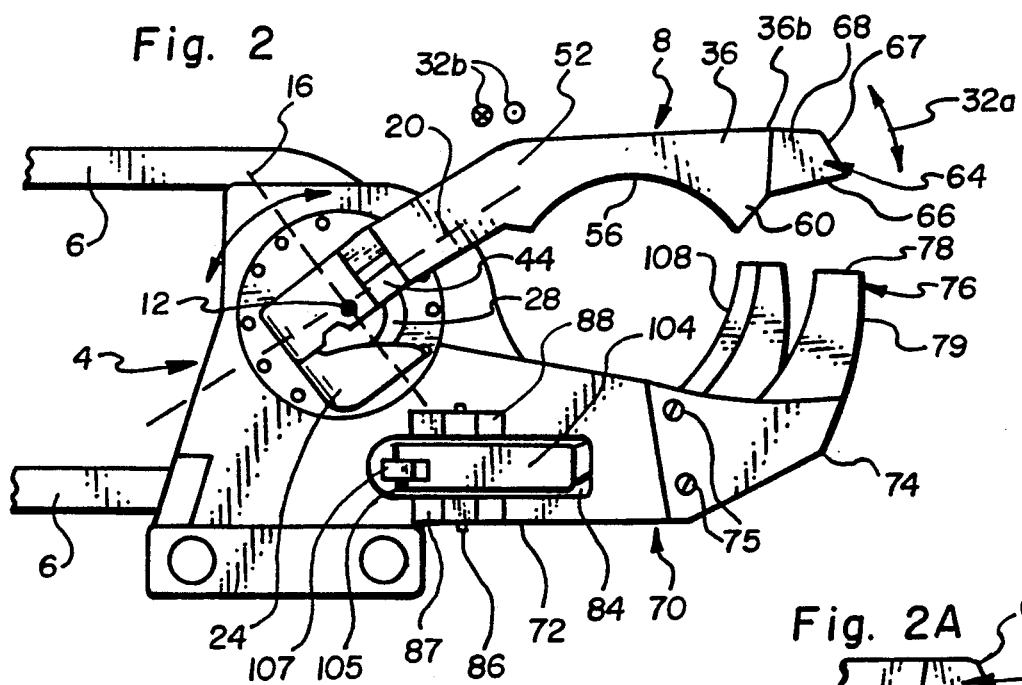
FIG. 2 is a side, elevational view of the apparatus of FIG. 1.
Figure 3:
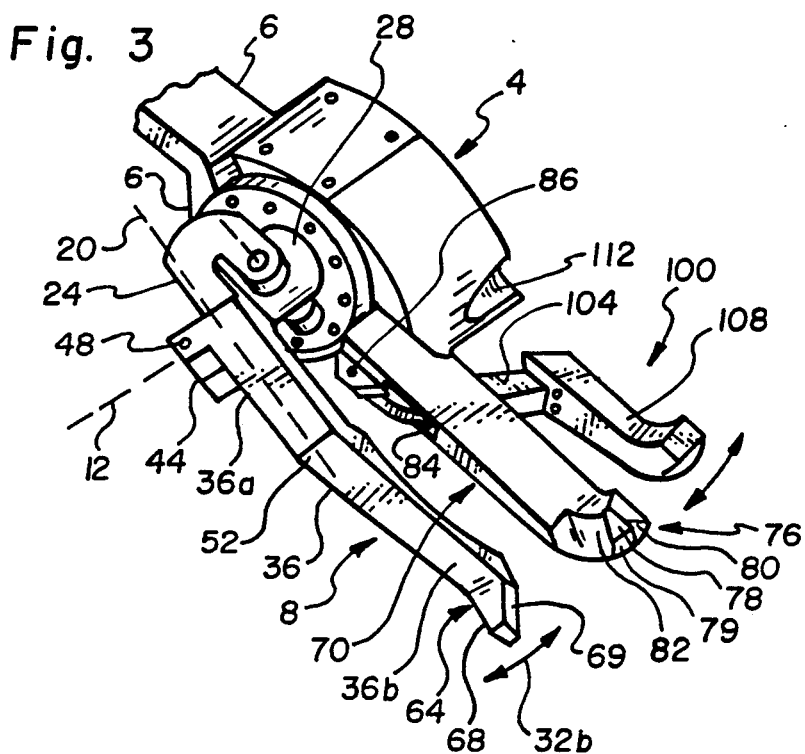
FIG. 3 is a top view of the apparatus of FIG. 1.

A thumb 8 is pivotally joined to the base 4 to pivot about two axes 12 and 16 (FIGS. 2 and 3) both of which extend laterally of the long axis 20 of the thumb and each of which is oriented generally at a right angle to the other. The pivoting mechanism of the thumb 8 includes a yoke 24 which pivots about axis 16 and which is mounted on an axle 28 which, in turn, is rotatably fixed in the base 4 to pivot about axis 12 (FIGS. 2 and 3). This provides the thumb 8 with two degrees of freedom of movement as indicated by arrows 32a and 32b (FIGS. 1 and 2). Mounting the thumb 8, as described, involves standard mounting technique and structure.

The thumb 8 further comprises an elongate, partially angled bar 36 having a fixed or base end 36a and a free end 36b. The fixed end 36a includes a servoclamp 44 for receiving a lug 40 projecting from the yoke 24. The bar 36 is mounted on the yoke 24 by placing the servoclamp 44 on the lug 40 and then tightening the clamp by a bolt 48 to thereby secure the thumb 8 on the lug 40, all in a conventional manner.

The bar 36 extends from the base end 36a a certain distance to an elbow 52 and then from the elbow at a slight angle to the free end 36b. Formed on the bottom side of the bar 36 just forwardly of the elbow 52 is a partly circular surface 56. A spur 60 projects downwardly from the underside of the bar 36 between the partly circular surface 56 and a tip 64 at the free end 36b of the bar. The thumb 8 is moveable so that the tip 64 may make contact at several surfaces with surfaces of a fixed or index finger 70 and a moveable finger 100, to next be discussed.

Figure 2A:
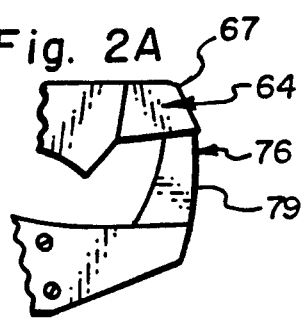
FIG. 2A is a side, partially fragmented view of the thumb and fixed index finger of the apparatus of FIG. 1.

The fixed or index finger 70 extends from the base 4 forwardly with a middle section 72 and then curves upwardly with an end section 74. The end section 74 includes a tip 76 formed with a number of surface areas to mate with certain surface areas of the tip 64 of the thumb 8. In particular, a bottom side 66 of the tip 64 of the thumb is shaped to contact and mate with a top side 78 of the tip 76 over a mutually extensive surface area when the thumb is pivoted downwardly onto the tip 76. When the thumb 8 is pivoted down onto the top side 78 of the index finger 70, a distal surface 67 of the thumb and a distal surface or outermost side 79 of the index finger are formed to be coplanar with one another at the point of contact between the thumb and index finger and are thus continuous, without break from one surface to the other. The surfaces 67 and 79 are generally convex, as best seen in FIG. 2A, to facilitate grasping or seizing of small objects between the thumb and index finger from a flat surface, for example.

A lateral side 68 of the tip 64 of the thumb 8 is shaped to contact a lateral side 80 of the tip 76 of the index finger 70 over a mutually extensive surface area, when the thumb is pivoted laterally to a position in contact with the side 80 of the index finger. This, of course, allows for grasping objects between the surface area 68 and surface area 80.

Figure 3A:
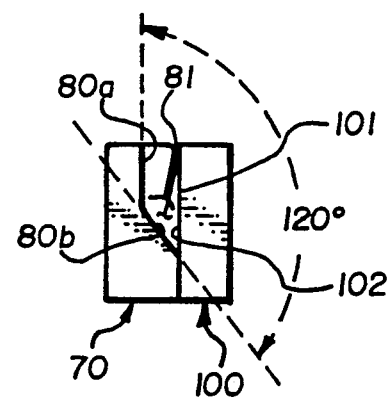
FIG. 3A is an end view of the thumb, index finger, and moveable finger positioned together.

The surface area 80 of the index finger 70 is also formed with a cutout portion 81, as best seen in FIG. 3A, to define two generally flat surface portions 80a and 80b which form an angle of 120° with respect to one another. Facing surface 102 of the finger 100 is formed to be generally parallel with surface portion 80a to allow for gripping a hexagon nut or bolt head between the index finger 70 and moveable finger 100, with two adjacent sides of such a nut or bolt being placed against surface portion 80a and 80b of the index finger 70, and another side being placed against surface 102 of moveable finger 100. The cutout portion 81 also accommodates the tip 64 of the thumb between the index finger 70 and the moveable finger 100.

Another lateral side 69 of the tip 64 of the thumb 8 (FIGS. 3 and 4) is shaped to contact lateral side 82 of the tip 76 of the index finger 70 over mutually extensive surface areas, when the thumb is pivoted laterally to a position in contact with the side 82. Again, objects may thus be held between the thumb 8 and side 82 of the index finger.

The moveable finger 100 is pivotally mounted in the middle section 72 of the index finger 70, near or at the base 40, to move laterally away from and toward the index finger. An opening 84 is formed in the middle section 72 to receive a proximal end 104 of the moveable finger 100 which is pivotally mounted on a pin 86 which extends between two ears 87 and 88 which, in turn, project generally in parallel from the side of the index finger 70 opposite that on which the moveable finger is positioned.

Figure 4:
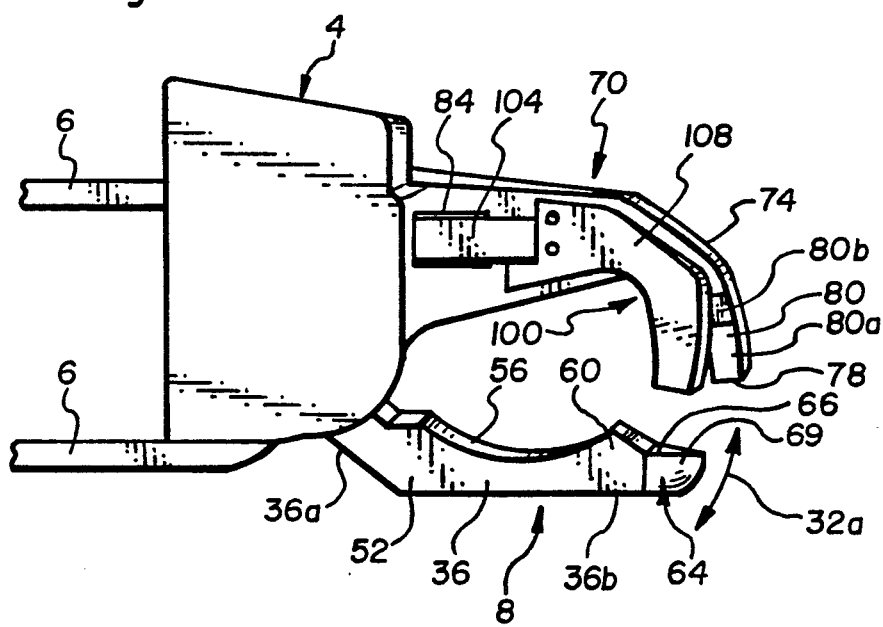
FIG. 4 is a side, elevational view of the apparatus showing the side opposite of that shown in FIG. 2.

The moveable finger 100 includes a free end 108 which extends from the proximal end 104 generally parallel with the index finger 70. The free end 108 of the moveable finger 100 is formed to curve along side of the end section 74 of the index finger 70 as best seen in FIGS. 1 and 4. The tip of the free end 108 of the moveable finger 100 is formed to contact and mate with the underside 66 of the tip 64 of the thumb 8, to hold objects therebetween. The thumb 8 is thus moveable over a range to mate with the ends or tips of the index finger 70 and the moveable finger 100. When the moveable finger 100 is pivoted against the index finger 70, a cutout portion or notch 81 between the moveable finger and index finger allows for pivoting the tip 64 of the thumb 8 therebetween, as indicated earlier (FIG. 3A).

As with the thumb 8, portions of the index finger 70 and moveable finger 100 may be removed and reattached as needed. Specifically, the end section 74 of the index finger may be removed by simply unscrewing set screws 75 which extend through openings in the end section and corresponding openings in a projection 73 of the middle section 72, when the projection 73 is fitted into a notch or groove 77 formed in the end section 74. When the set screws 75 are removed, the end section 74 may simply be removed from the middle section 72 and serviced, replaced, etc. In a similar fashion, the free end 108 of the moveable finger 100 is detachably mounted on the proximal end 104 of the finger.

Effecting pivoting of the thumb 8 and moveable finger 100 may be carried out in any conventional fashion. For example, the proximal end 104 of the finger 100 may be formed with a fork 105 (FIGS. 1 and 2), between which is pivotally mounted a push rod 107 for pushing or pulling on the fork to cause the finger to pivot. Pivoting of the thumb 8 could be controlled in a similar fashion, with the controlling mechanisms located in the base 4.

With the apparatus of FIGS. 1–4, a versatile grasping and holding robotic implement is provided. This apparatus utilizes a single fixed finger, a one degree of freedom of movement moveable finger, and a two degree of freedom of the movement thumb to provide for grasping and holding a variety of different shaped objects. To accommodate holding elongate objects, a groove 112 is formed in the base housing (palm) 112. As will be discussed later, an elongate object placed between the thumb 8, on one side, and the fingers 70 and 100, on the other side, would also rest in the groove 112.

Figure 5:
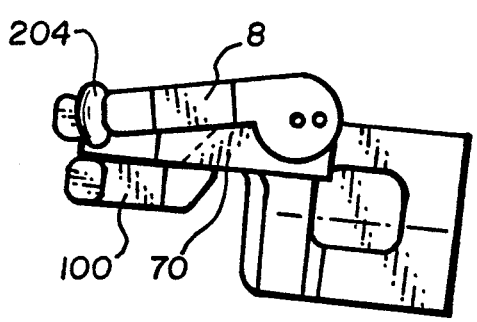
FIG. 5 is a graphic representation of the apparatus in a two point pinch hold of a small object between the thumb and index finger.

FIGS. 5–14 are graphic representations of the apparatus of FIGS. 1–4 illustrating various objects which can be grasped and the manner in which they can be grasped. FIG. 5 shows a two-point pinch grasp in which a small three dimensional object 204 is held between the thumb 8 and index finger 70 in a manner similar to a human hand pinching an object between the index finger and opposing thumb. This grasp is effective for picking up and holding small objects.

Figure 6:
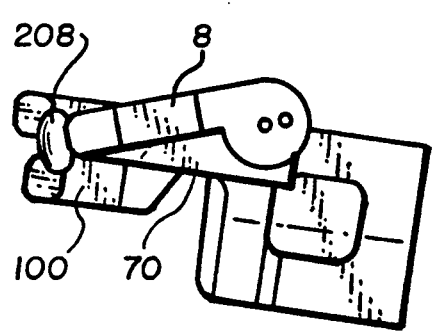
FIG. 6 is a graphic representation of the apparatus in three point pinch hold of a small object between the thumb, index finger and moveable finger.

FIG. 6 shows a three-point pinch grasp in which an object 208 is held between the thumb 8, index finger 70, and moveable finger 100. This grasp is similar to a human hand pinching an object using the index finger, middle finger and opposing thumb. This grasp is a somewhat more stable way of holding larger objects than that shown in the FIG. 5 grasp (even though the object shown in FIG. 6 is the same size as that shown in FIG. 5).

Figure 7:
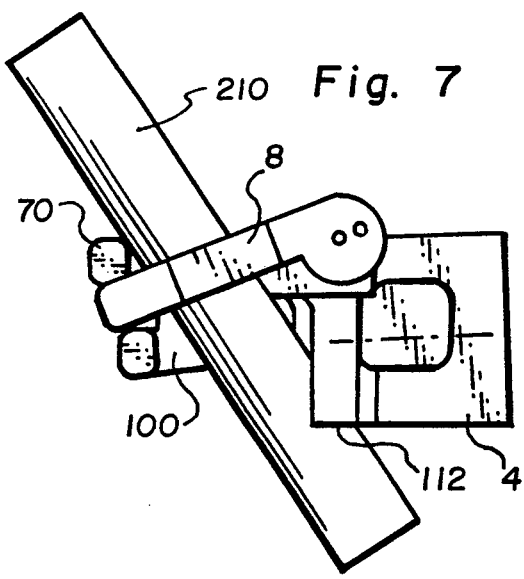
FIG. 7 is a graphic representation of the apparatus holding an elongate bar.

FIG. 7 shows a wrap grasp in which a bar 210 is held between the index finger 70 and moveable finger 100 on one side and the thumb 8 on the other side, with the bar being further constrained by the groove 112 in the base 4. Tools and implements having handles, such as hammers, hose, shovels, etc., may be held with the wrap grasp shown in FIG. 7.

Figure 8:
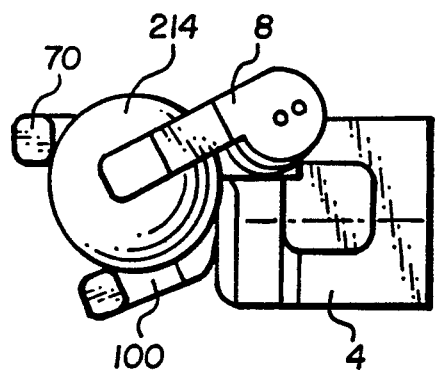
FIG. 8 is a graphic representation of the apparatus holding a ball.

FIG. 8 shows a spherical grasp in which a ball 214 is held between the two fingers and thumb, but more rearwardly (and against the base 4) than with the three-point pinch of FIG. 6.

Figure 9:
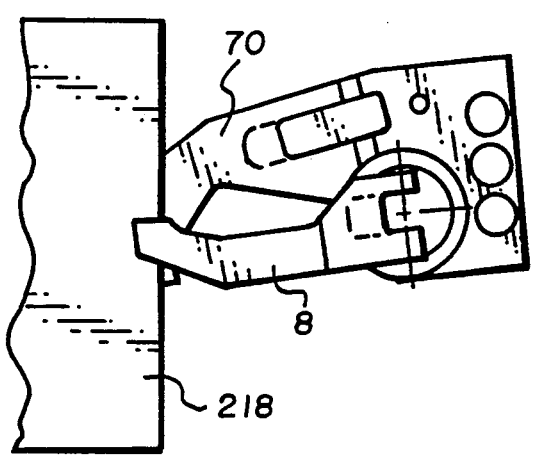
FIG. 9 is a graphic representation of the apparatus holding a thin sheet between the thumb and index finger.

FIG. 9 shows a lateral-pinch grasp in which a sheet of material, file folder, and the like is held between the index finger 70 and the thumb 8, with the thumb pressing the object against the side of the index finger. This grasp is especially suitable for holding cards or other flat articles when such cards are to be inserted into and removed from locations where the edges of the cards are accessible.

Figure 10:
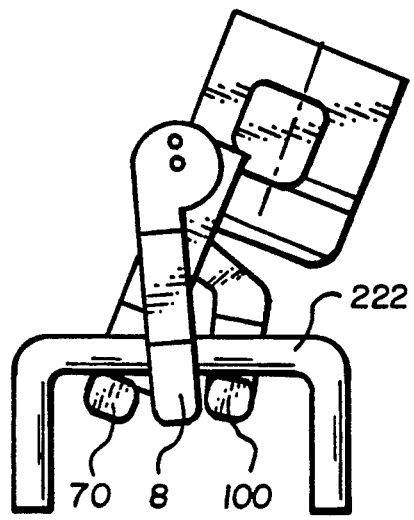
FIG. 10 is a graphic representation of the apparatus holding a handle such as a suitcase handle.

FIG. 10 shows a type of loop grasp, for holding suitcase handles, mug handles, telephone receivers, etc., in which a handle 222 is held by the thumb 8 against the curved free end portions of the index finger 70 and moveable finger 100. With this grasp, the loads are supported by the index finger and moveable finger and so the lifting capability is independent of the clamping force provided by the thumb 8.

Figure 11:
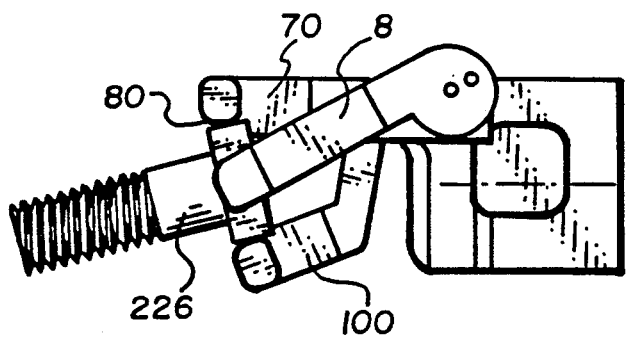
FIG. 11 is a graphic representation of the apparatus holding the head of a bolt.

FIG. 11 shows the grasping apparatus holding the hexagonal-side head of a bolt, where two sides of the head are positioned against surface portions 80a and 80b of the index finger 70. The head of the bolt 226 is also held by the free or distal ends of the fingers 100 and thumb 8 which are positioned against other respective other sides of the bolt head.

Figure 12:
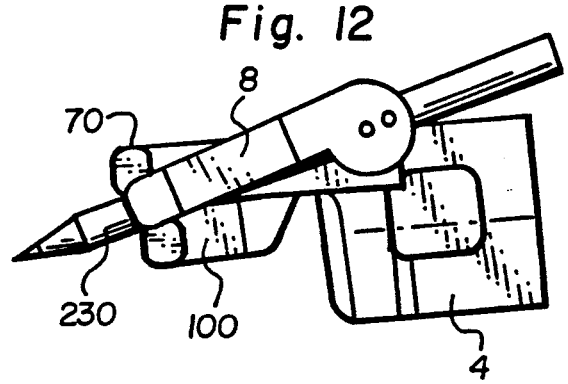
FIG. 12 is a graphic representation of the apparatus holding a pencil.

FIG. 12, as is clear from the figure, shows a pencil/pen grasp in which a pencil or pen 230 is held near the writing end between the thumb 8, index finger 70 and moveable finger 100, with the rear end of the pen or pencil extending rearwardly over the base 4 of the apparatus.

Figure 13:
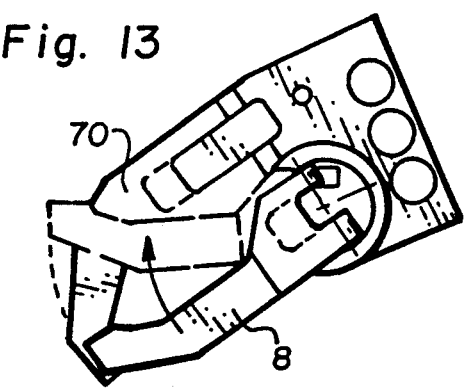
FIG. 13 is a graphic representation of the apparatus illustrating a thumb slide operation.

FIG. 13 shows a thumb-slide operation in which the thumb 8 is moved in a sliding motion over one side of the index finger 70. This operation might be used to start nuts on bolts, threading fasteners together, and similar objects where a human index finger-sliding over the thumb motion is required.

Figure 14:
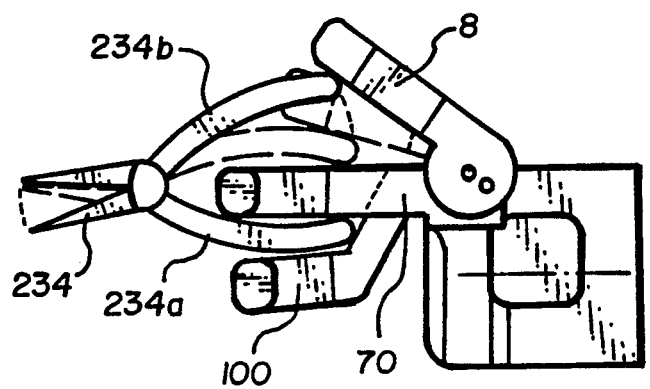
FIG. 14 is a graphic representation of the apparatus holding a pair of pliers.

FIG. 14 shows the grasping apparatus of the present invention holding the handles of a pair of pliers 234. As shown, handle 234a of the pliers is held securely between the index finger 70 and moveable finger 100, while the thumb 8 may be moved to press the other handle 234b of the pliers downwardly to close the pliers.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. Grasping apparatus comprising a fixed finger having a base section, a narrowed middle section extending outwardly from the base section, and a curved end section which extends outwardly and upwardly from the middle section to terminate in a tip having first and second lateral sides, an outermost side, and an end, an elongate moveable thumb having a fixed end mounted in the base of the finger to pivot about a first axis which extends laterally of the long axis of the thumb, and to rotate about a second axis extending generally perpendicular to the base of the finger and being generally coaxial with the rotation of the thumb when the thumb is extended, and a free end selectively moveable to a position in contact with the end of said tip and to a position in contact with the lateral sides of said tip, wherein said free end has first and second lateral sides, a bottom side, and a distal surface, wherein the bottom side of the free end of the thumb, and the end of said tip are formed with conformable contact surfaces, and wherein the distal surface of the free end of the thumb and the surface of the outermost side of the tip of the finger form a continuous unbroken surface when the bottom side of the thumb and the end of the tip are in contact.

2. Grasping apparatus as in claim 1 wherein the distal surface of the free end of the thumb and the surface of the outermost side of the tip of the finger are generally convex.

3. Grasping apparatus as in claim 1 wherein the first lateral side of the free end of the thumb and the second lateral side of the tip are formed with conformable contact surfaces.

4. Grasping apparatus as in claim 3 wherein the second lateral side of the free end of the thumb and the first lateral side of the tip are formed with conformable contact surfaces.

5. Grasping apparatus as in claim 1 wherein said end section of the finger is formed so that the tip is generally at a right angle with respect to the middle section.

6. Grasping apparatus as in claim 1 wherein said thumb is mounted so that the free end may be moved downwardly to contact the end of said tip, upwardly away from the end of said tip, laterally toward the second lateral side of the tip, laterally away from said second lateral side of the tip, laterally toward the first lateral side of the tip, and laterally away from the first lateral side of the tip.

7. Grasping apparatus as in claim 1 wherein a bottom side of the thumb rearwardly of the free end, generally faces the fixed finger and is formed with a generally concave surface area.

8. Grasping apparatus as in claim 7 wherein said concave surface area is generally a circular segment.

9. Grasping apparatus as in claim 1 wherein the end section of the fixed finger is removeably mounted on the middle section of the finger.

10. Grasping apparatus as in claim 1 wherein the free end of the thumb is removeably mounted on the fixed end of the thumb.

11. Grasping apparatus as in claim 1 further comprising a moveable finger pivotally mounted to the fixed finger at a base end to pivot a free end toward and away from the end section of the fixed finger, to make contact therewith.

12. Grasping apparatus as in claim 11 wherein said moveable finger is mounted to pivot in a plane laterally against one side of the fixed finger, and away from the fixed finger.

* * * * *